United States Patent [19]

Fukuma et al.

[11] Patent Number: 4,810,085
[45] Date of Patent: Mar. 7, 1989

[54] CORNEAL CONFIGURATION MEASURING APPARATUS

[75] Inventors: Yasufumi Fukuma; Yoshinori Oana; Akihiro Arai, all of Tokyo, Japan

[73] Assignee: Tokyo Kogaku Kikai Kabushiki Kaisha, Tokyo, Japan

[21] Appl. No.: 69,200

[22] Filed: Jul. 2, 1987

[30] Foreign Application Priority Data

Jul. 4, 1986 [JP] Japan .................................. 61-157478

[51] Int. Cl.$^4$ .............................................. A61B 3/10
[52] U.S. Cl. ...................................... 351/212; 351/247
[58] Field of Search ................................ 351/212, 247

[56] References Cited

U.S. PATENT DOCUMENTS 2,733,634  2/1956  Littman et al. ...................... 351/212
3,639,043  2/1972  Townsley ............................ 351/212
3,640,610  2/1972  Nupuf ................................. 351/212
4,660,946  4/1987  Nakamura ........................... 351/212

Primary Examiner—Rodney B. Bovernick
Attorney, Agent, or Firm—Finnegan, Henderson, Farabow, Garrett & Dunner

[57] ABSTRACT

A corneal configuration measuring apparatus is disclosed. It comprises target projecting means for projecting target beams from a plurality of targets towards a cornea of an eye to be tested, light receiving means, measuring optical system for projecting the target beams reflected on the cornea towards the light receiving means and forming target reflection images on the light receiving means, and variable power optical system for varying imaging power of the target reflection images to be formed on the light receiving means.

14 Claims, 2 Drawing Sheets

F I G. 2
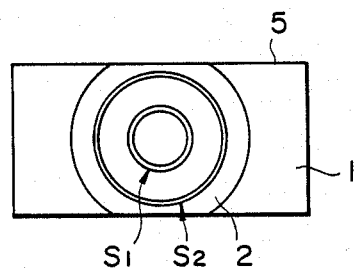
F I G. 3
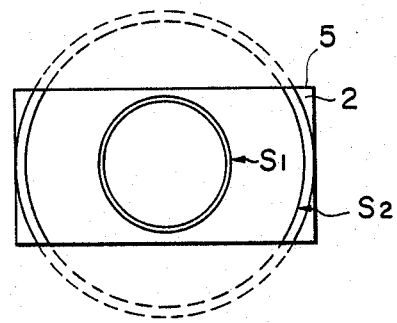

CORNEAL CONFIGURATION MEASURING APPARATUS

BACKGROUND OF THE INVENTION

This invention relates to a corneal configuration measuring apparatus for measuring a corneal configuration such as the radius of curvature of a cornea of a patient.

Heretofore, there has been known a corneal configuration measuring apparatus for measuring a corneal configuration of a patient in which a plurality of concentric measuring target beams about the optical axis of an eye to be tested are projected from a light source towards a patient's cornea, and a plurality of corneal reflection images of the measuring target beams which are imaged by a specular reflection on the cornea are projected to a light receiving portion for detecting an optical information in order to measure the corneal configuration of the patient based on the optical information of various corneal reflection images detected by the light receiving portion.

However, the conventional apparatus has the problem in that when a plurality of corneal reflection images of the measuring target beams which have been specular reflected on the cornea are projected to a light receiving portion, since a corneal reflection image in the vicinity of the optical axis of the eye to be tested of the cornea among the plurality of corneal reflection images of the measuring target beams is tiny, an accurate measurement of the corneal configuration thereof is difficult to obtain compared with the corneal configuration far from the optical axis of the eye to be tested.

SUMMARY OF THE INVENTION

The present invention was accomplished in view of the above-described problem. It is therefore an object of the present invention to provide a corneal configuration measuring apparatus in which the corneal configuration of an cornea at a portion in the vicinity of the optical axis of the eye to be tested can be equally accurately measured as the corneal configuration at a portion far from the optical axis.

In order to achieve the above object, there is essentially provided a corneal configuration measuring apparatus comprising target projecting means for projecting target beams from a plurality of targets towards a cornea of an eye to be tested, light receiving means, measuring optical system for projecting the target beams reflected on the cornea towards the light receiving means and forming target reflection images on the light receiving means, and variable power optical system for varying imaging power of the target reflection images to be formed on the light receiving means.

According to the corneal configuration measuring apparatus of the present invention, the corneal reflection images which have been projected to the light receiving portion by the variable power optical system disposed in the measuring optical system are enlarged so that even the corneal configuration of the cornea at a portion in the vicinity of the optical axis of an eye to be tested can be accurately measured.

BRIEF DESCRIPTION OF THE DRAWINGS

The afore-described and other objects, characteristic features and advantages of the present invention will become apparent to those skilled in the art from the following detailed description of the embodiment taken in conjunction with the accompanying drawings, in which:

FIG. 2 is an illustration for explaining a projecting state of corneal reflection images which have been projected to a light receiving portion through a low power imaging lens according to one embodiment of the present invention; and FIG. 3 is an illustration for explaining a projecting state of corneal reflection images which have been projected to the light receiving portion through a high power imaging lens according to one embodiment of the present invention.

DETAILED DESCRIPTION OF THE EMBODIMENT

Figure 1:
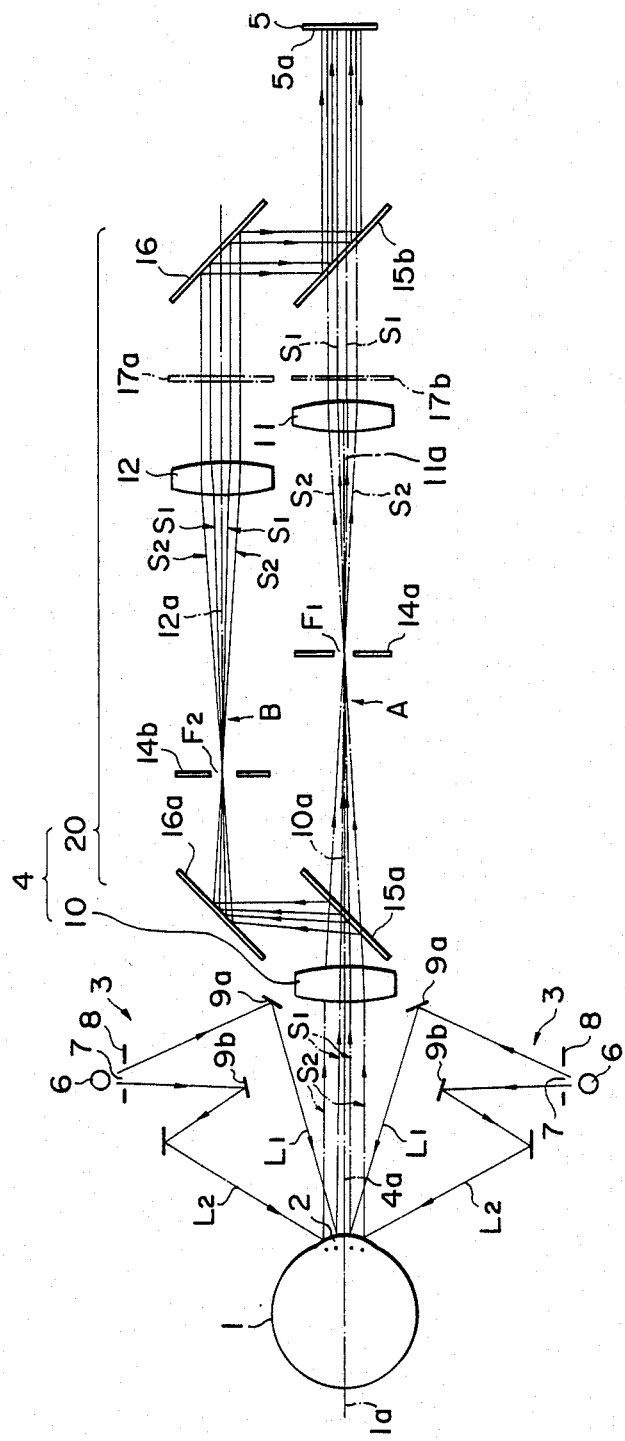
FIG. 1 is a schematic view showing the constitution of a corneal configuration measuring apparatus according to one embodiment of the present invention.

One preferred embodiment of a corneal configuration measuring apparatus will be described hereunder with reference to the accompanying drawings.

FIG. 1 is a schematic view showing the constitution of a corneal configuration measuring apparatus according to one embodiment of the present invention. The corneal configuration measuring apparatus generally comprises a projecting optical system 3 for projecting target beams $L_1$ and $L_2$ to a cornea 2 of a patient's eye 1 to be tested, a measuring optical system 4 disposed adjacent to the cornea 2 and adapted to power vary the corneal reflection images $S_1$ and $S_2$ which have been specular reflected by the cornea 2, and a light receiving portion 5 for detecting the corneal reflection images $S_1$ and $S_2$ which have been power varied by the measuring optical system 4 and obtaining an optical information regarding the cornea 2.

The projecting optical system 3 is symmetrically disposed with the optical axis 4a of the measuring optical system 4. The light receiving portion 5 is coaxially disposed with the optical axis 4a. In this embodiment, the projecting optical system 3 includes a light source 6, a slit plate 8 having a slit 7, and reflection mirrors 9a and 9b. The projecting optical system 3 is disposed in the peripheral direction about the optical axis 4a. The light source 6, the slit 7, the slit plate 8, and the reflection mirrors 9a and 9b are formed in a ring-shape, respectively. The reflecting surfaces of the reflection mirrors 9a and 9b each has a parabolic configuration in section within a plane including the optical ais 4a serving the slit 7 as a focus. The beams radiated from the light source 6 passing through the slit 7 are projected in parallel relation towards the cornea 2. More specifically, the target beams $L_1$ and $L_2$ which are to be projected to the outer surface of the cornea 2 are obtained by making the beams radiated from the slit 7 form concentric circles about the optical axis 4a by means of the reflection mirrors 9a and 9b.

The measuring optical system 4 comprises an objective lens 10 and a variable power optical system 20. The objective lens 10 is disposed in front of the cornea 2. The optical axis 4a of the measuring optical system 4 is in alignment with the optical axis 10a of the objective lens 10.

In this embodiment, the variable power optical system 20 includes a lower power optical path A and a high power optical path B. The low power optical path A comprises an objective lens 10, a telecentric diaphragm 14a, half mirrors 15a and 15b, a low power imaging lens 11, etc., whereas the high power optical path B comprises an objective lens 10, a telecentric diaphragm 14b, half mirrors 15a and 15b, reflection mirrors 16a and 16b, a high power imaging lens 12, etc.

The low power imaging lens 11 is provided as such that the position of the telecentric diaphragm 14a becomes the front focus. The telecentric diaphragm 14a is disposed at the rear focus of the objective lens 10.

The focussing distance of the low power imaging lens 11 at the light receiving portion 5 is set to be as the distance where the corneal reflection images $S_1$ and $S_2$ from the low power optical path A are imaged on the front surface 5a of the light receiving portion 5. When the corneal reflection images $S_1$ and $S_2$ are projected through the low power optical path A, the entire corneal reflection images $S_1$ and $S_2$ from the objective lens 10 are projected to the light receiving portion 5 as shown in FIG. 2.

The high power imaging lens 12 has an optical axis 12a parallel to the optical axis 10a of the objective lens 10 so that the high power optical path B at the high power imaging lens 12 is formed separated apart from the low power optical path A at the low power imaging lens 11. The high power imaging lens 12 is disposed as such that the position of the telecentric diaphragm 14b will become the front side focus. The telecentric diaphragm 14b is disposed in a position where it becomes the rear side focus of the objective lens 10.

The high power imaging lens 12 is set as such that the corneal reflection images $S_1$ and $S_2$ reflected by the reflection mirror 15a are projected to the light receiving portion 5 in an enlarged scale as shown in FIG. 3. The optical path selecting means comprises liquid crystal shutters 17a and 17b which are opened and shut in turn.

A half mirror 15a as an optical path diverging means is disposed between the telecentric diaphragm 14a of the focussing position of the objective lens 10 and the objective lens 10 in the vicinity of the objective lens 10, so that the corneal reflection images $S_1$ and $S_2$ from the objective lens 10 are reflected by the half mirror 15a and projected to the reflection mirror 16a opposite to the half mirror 15a.

The reflection mirror 16a is disposed as such that the corneal reflection images $S_1$ and $S_2$ reflected by the half mirror 15a are reflected in the direction of the extension of the optical axis 12a. $F_2$ is provided with the telecentric diaphragm 14b.

At the light receiving portion 5 side of the optical axis 12a of the high power imaging lens 12, a liquid crystal shutter 17a and a reflection mirror 16b are disposed. The liquid crystal shutter 17a is associated with the movement of a liquid crystal shutter 17b disposed on the optical axis 11a at the low power imaging lens 11 side so that when the liquid crystal shutter 17b shut the low power optical path A at the low power imaging lens 11 side, the high power optical path B at the high power imaging lens 12 side is opened. The reflection mirror 16b is disposed on the optical axis 12a of the high power imaging lens 12 and opposite to the half mirror 15b as the optical path composing means disposed on the optical axis 11a of the low power imaging lens 11 so that the corneal reflection images $S_1$ and $S_2$ which have passed the high power imaging lens 12 are reflected by the half mirror 15b. The liquid crystal shutter 17b and the half mirror 15b are disposed at the light receiving portion 5 side of the low power imaging lens 11, the liquid crystal shutter 17b is disposed in the vicinity of the low power imaging lens 11, and the half mirror 15b is disposed between the liquid crystal shutter 17b and the light receiving portion 5. Instead of the liquid crystal shutters 17a and 17b, mechanical shutters which are associated with the movement with each other may be used.

In this embodiment, the light receiving portion 5 is used an area CCD as a two-dimensional solid state image pickup device and connected with a calculating apparatus (not shown). In the light receiving portion 5, in the case where the liquid crystal shutter 17b is opened thereby to open only the low power optical path A, optical information regarding the entire configuration (radius of curvature) of the cornea 2 is detected, whereas in the case where the liquid crystal shutter 17a is opened thereby to open only the high power optical path B, optical information regarding the configuration (radius of curvature) of the cornea 2 is detected at a portion in the vicinity of the optical axis of the eye 2a to be tested. The light receiving portion 5 is disposed in a position where the corneal reflection images $S_1$ and $S_2$ from the low power imaging lens 11 and the enlarged corneal reflection images $S_1$ and $S_2$ from the high power imaging lens 12 are formed.

More specifically, the distance from the high power imaging lens 12 to the front surface 5a of the light receiving portion 5 through the reflection mirror 16b and the half mirror 15b is set as the distance in which the corneal reflection images $S_1$ and $S_2$ which are to be entered into the high power imaging lens 12 are formed on the front surface 5a of the light receiving portion 5, whereas the distance from the low power imaging lens 11 to the front surface 5a of the light receiving portion 5 through the half mirror 15b is set to be the distance in which the corneal reflection images $S_1$ and $S_2$ which are to be entered into the low power imaging lens 11 are formed on the front surface 5a of the light receiving portion 5.

In this embodiment, the liquid crystal shutters 17a and 17b are opened and shut in turn to switch the low power optical path A and the high power optical path B with each other. However, instead of the liquid crystal shutters 17a and 17b, the optical paths may be switched by allowing the half mirrors 15a and 15b to associate with the movement of reflection type quick return mirrors. In that case, the quick return mirrors constitute the first and second optical path selecting means, respectively. Thus, the low power optical path A and the high power optical path B can be switched with each other. In addition, the corneal reflection beams which have been reflected by the half mirrors 15a and 15b can be prevented from becoming weak.

As described in the foregoing, the corneal configuration measuring apparatus according to the present invention comprises a measuring optical system disposed between an objective lens optical system and a light receiving portion and adapted to vary the power of multiple corneal reflection images. Accordingly, the corneal reflection images which are projected to the light receiving portion can be enlarged. Thus, the configuration of the cornea at a portion in the vicinity of the optical axis of the eye to be tested can be as accurately measured as the corneal configuration at a portion far from the optical axis of the eye to be tested.

From the foregoing description on the preferred embodiment of the present invention referring to the accompanying drawings, various modification and changes in constitution will easily occur to those having ordinary knowledge in the art and furthermore, the present invention may be embodied in substantially similar modes which fulfill substantially the same purpose and attain substantially the same effects as those described in connection with the preferred embodiment.

What is claimed is:

1. A corneal configuration measuring apparatus comprising:
   target projecting means for projecting target beams from a plurality of targets towards a cornea of an eye to be tested, said cornea having an optical axis; light receiving means;
   measuring optical system means for projecting the target means reflected on the cornea towards said light receiving means and for forming target reflection images on said light receiving means; and
   variable power optical system means for varying imaging power of said target reflection images such that target reflection images corresponding to portions of the cornea proximate to said optical axis may be imaged at a higher power relative to target reflection images corresponding to portions of the cornea spaced from said optical axis.

2. A corneal configuration measuring apparatus, comprising:
   target projecting means for projecting target beams from a plurality of targets towards a cornea of an eye to be tested, said cornea having an optical axis; light receiving means;
   measuring optical system means for projecting the target beams reflected on the cornea towards said light receiving means and for forming target reflection images on said light receiving means;
   variable power optical system means for varying imaging power of said target reflection images such that target reflection images corresponding to portions of the cornea proximate to said optical axis may be imaged at a higher power relative to target reflection images corresponding to portions of the cornea spaced from said optical axis; and
   wherein said measuring optical system comprises a low power optical path for projecting and imaging said target reflection images on said light receiving means at low power, a high power optical path for projecting and imaging said target reflection images on said light receiving means at a high power, and optical path selecting means for selecting an optical path so that said target reflection images will be projected and imaged on said light receiving means through one of said low power optical path and high power optical path.

3. A corneal configuration measuring apparatus as claimed in claim 2, wherein said measuring optical system includes a common objective lens, optical path diverging means disposed behind said common objective lens and adapted to enter said reflection beams from said common objective lens into both said low and high power optical paths, and optical path composing means disposed in front of said light receiving means and adapted to compose said low and high power optical paths, and said optical path selecting means includes shutter means for opening one of said low and high power optical paths between said optical path diverging means and said optical path composing means and closing the other optical path.

4. A corneal configuration measuring apparatus as claimed in claim 3, wherein said shutter means is a liquid crystal shutter.

5. A corneal configuration measuring apparatus as claimed in claim 3, wherein said optical path diverging means and said optical path composing means include a half mirror.

6. A corneal configuration measuring apparatus as claimed in claim 2, wherein said measuring optical system includes a common objective lens, first optical path selecting means disposed behind said common objective lens and adapted to selectively enter said reflection beams from said common objective lens into one of said low and high power optical paths, and second optical path selecting means disposed in front of said light receiving means and adapted to selectively enter one of said reflection beams which has passed through said lower power optical path or high power optical path into said light receiving means in association with the movement of said first optical path selecting means.

7. A corneal configuration measuring apparatus as claimed in claim 6, wherein said first and second optical path selecting means is a quick return mirror.

8. A corneal configuration measuring apparatus as claimed in claim 3, wherein said low power optical path includes a low power imaging lens having a front side focus, said high power optical path includes a high power imaging lens having a front side focus, and said common objective lens has a rear side focus, said front side focuses of said low and high power imaging lenses being positioned at said rear side focus.

9. A corneal configuration measuring apparatus as claimed in claim 8, wherein a telecentric diaphragm is disposed at said rear side focus.

10. A corneal configuration measuring apparatus as claimed in claim 6, wherein said low power optical path includes a low power imaging lens having a front side focus, said high power optical path includes a high power imaging lens having a front side focus, and said common objective lens has a rear side focus, said front side focuses of said low and high power imaging lenses being positioned in said rear side focussing position.

11. A corneal configuration measuring apparatus as claimed in claim 10, wherein a telecentric diaphragm is disposed at said rear side focus.

12. A corneal configuration measuring apparatus as claimed in claim 2, wherein said target beams are comprised of a plurality of concentric circles, and said target projecting means includes means for projecting said target beams to said cornea in the form of parallel pencils of light beams.

13. A corneal configuration measuring apparatus as claimed in claim 2, wherein said light receiving means includes a two-dimensional image-pickup means.

14. A corneal configuration measuring apparatus as claimed in claim 13, wherein said two-dimensional image-pickup means is an area CCD.

* * * * *